United States Patent
Jang et al.

(10) Patent No.: US 8,126,557 B2
(45) Date of Patent: Feb. 28, 2012

(54) LEAD CONNECTOR PIN AND BODY ASSEMBLY AND METHOD OF MANUFACTURE

(75) Inventors: Grace Jang, Calabasas, CA (US); Phong D. Doan, Stevenson Ranch, CA (US); Steven R. Conger, Agua Dulce, CA (US)

(73) Assignee: Pacesetter, Inc., Sylmar, CA (US)

( * ) Notice: Subject to any disclaimer, the term of this patent is extended or adjusted under 35 U.S.C. 154(b) by 459 days.

(21) Appl. No.: 12/370,936

(22) Filed: Feb. 13, 2009

(65) Prior Publication Data

US 2010/0211144 A1 Aug. 19, 2010

(51) Int. Cl.
*A61N 1/00* (2006.01)
(52) U.S. Cl. .......................................... 607/37; 439/909
(58) Field of Classification Search .................... 607/37; 439/909
See application file for complete search history.

(56) References Cited

U.S. PATENT DOCUMENTS

| 4,898,173 A | 2/1990 | Daglow et al. |
| 4,934,367 A | 6/1990 | Daglow et al. |
| 7,305,267 B2 | 12/2007 | Hector |
| 2010/0137928 A1 * | 6/2010 | Duncan et al. .................... 607/5 |

FOREIGN PATENT DOCUMENTS

EP 0339877 A2 11/1989

* cited by examiner

*Primary Examiner* — Scott Getzow

(57) ABSTRACT

An implantable medical lead is disclosed herein. In one embodiment, the lead includes a body, at least one electrode and a lead connector end. The body includes a distal portion and a proximal portion. The at least one electrode is on the distal portion. The lead connector end is on the proximal portion and includes a pin contact and a retainer assembly. The pin contact is electrically coupled to the at least one electrode and proximally extends from the lead connector end. The retainer assembly retains the pin contact as part of the lead connector end and includes a collar and a cap. The cap is secured within the collar via an interference fit arrangement and includes a hole through which the pin contact extends.

26 Claims, 12 Drawing Sheets

LEAD CONNECTOR PIN AND BODY ASSEMBLY AND METHOD OF MANUFACTURE

FIELD OF THE INVENTION

The present invention relates to medical apparatus and methods. More specifically, the present invention relates to implantable medical leads and methods of manufacturing such leads.

BACKGROUND OF THE INVENTION

Implantable medical leads for use with implantable pulse generators, such as neurrostimulators, pacemakers, defibrillators or implantable cardioverter defibrillators ("ICD"), have lead connector ends on the proximal ends of the leads that are received in implantable pulse generators for mechanical and electrical connection to the implantable pulse generators. Lead connector ends often employ connector pins that are mechanically and electrically connected to an electrical conductor extending through the lead body to an electrode on the distal end of the lead body. For example, the connector pins may be electrically and mechanically connected to an inner helically coiled electrical conductor. Some such connector pins may need to be rotatable relative to the rest of the lead body to enable the helically coiled electrical conductor, which may be in electrical connection with a helical anchor electrode, to rotate relative to the rest of the lead body, thereby allowing the connector pin and helically coiled electrical conductor to be rotated to allow the helical anchor electrode to be screwed into cardiac tissue to secure the lead distal end to the implant site.

Current lead connector end configurations are expensive to assemble and provide tensile strength that is less than desired with respect to a connector pin being pulled from a lead connector end assembly.

There is a need in the art for a lead connector end assembly that offers improved tensile strength and reduced manufacturing costs. There is also a need in the art for methods of manufacturing and using such a lead connector end.

BRIEF SUMMARY OF THE INVENTION

An implantable medical lead is disclosed herein. In one embodiment, the lead includes a body, at least one electrode and a lead connector end. The body includes a distal portion and a proximal portion. The at least one electrode is on the distal portion. The lead connector end is on the proximal portion and includes a pin contact, a body portion and a retainer assembly. The pin contact is electrically coupled to the at least one electrode and proximally extends from the lead connector end. The body portion is at least partially formed of a polymer material. The retainer assembly retains the pin contact as part of the lead connector end and includes a collar and a cap. The collar is imbedded in the polymer material. The cap is secured within the collar via an interference fit arrangement and includes a hole through which the pin contact extends.

Another implantable medical lead is disclosed herein. In one embodiment, the lead includes a body, at least one electrode and a lead connector end. The body includes a distal portion and a proximal portion. The at least one electrode is on the distal portion. The lead connector end is on the proximal portion and includes a pin contact, a body portion and a retainer assembly. The pin contact is electrically coupled to the at least one electrode and proximally extends from the lead connector end. The body portion is at least partially formed of a polymer material. The retainer assembly retains the pin contact as part of the lead connector end and includes a collar and a cap. The collar is imbedded in the polymer material. The cap is secured within the collar via a weld and includes a hole through which the pin contact extends.

Yet another implantable medical lead is disclosed herein. In one embodiment, the lead includes a body, at least one electrode and a lead connector end. The body includes a distal portion and a proximal portion. The at least one electrode is on the distal portion. The lead connector end is on the proximal portion and includes a pin contact, a body portion and a retainer assembly. The pin contact is electrically coupled to the at least one electrode and proximally extends from the lead connector end. The body portion is at least partially formed of a polymer material. The retainer assembly retains the pin contact as part of the lead connector end and includes a cap. The cap is operably coupled to the polymer material via a threaded arrangement and includes a hole through which the pin contact extends. In one embodiment, the retainer assembly further includes a collar imbedded in the polymer material and having threads that threadably engage threads on the cap. In another embodiment, there is no collar, the cap instead having self-tapping threads that thread directly into the polymer material.

A method of assembling a lead connector end for an implantable medical lead is disclosed herein. In one embodiment the method includes: providing a lead connector end including a body portion at least partially formed of a polymer material and a collar imbedded in the polymer material; providing a cap including at least one feature configured to create an interference fit with at least one feature of the collar; inserting a pin contact through a hole in the cap; and creating the interference fit between the cap and collar by inserting the cap into the collar.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

An implantable medical lead 10 is disclosed herein. The lead 10 includes a novel connector pin assembly 120 that reduces assembly time and costs and results in a secure and strong attachment of the pin contact 55 to the rest of the lead connector end 35. In some embodiments, the connector pin assembly 120 may be configured to allow the pin contact 55 to rotate relative to the rest of the connector pin assembly 120 and the rest of the lead connector end 35. In other embodiments, the connector pin assembly 120 may be configured such that the pin contact 55 will not rotate relative to the rest of connector pin assembly 120 or the rest of the lead connector end 35.

Figure 1:
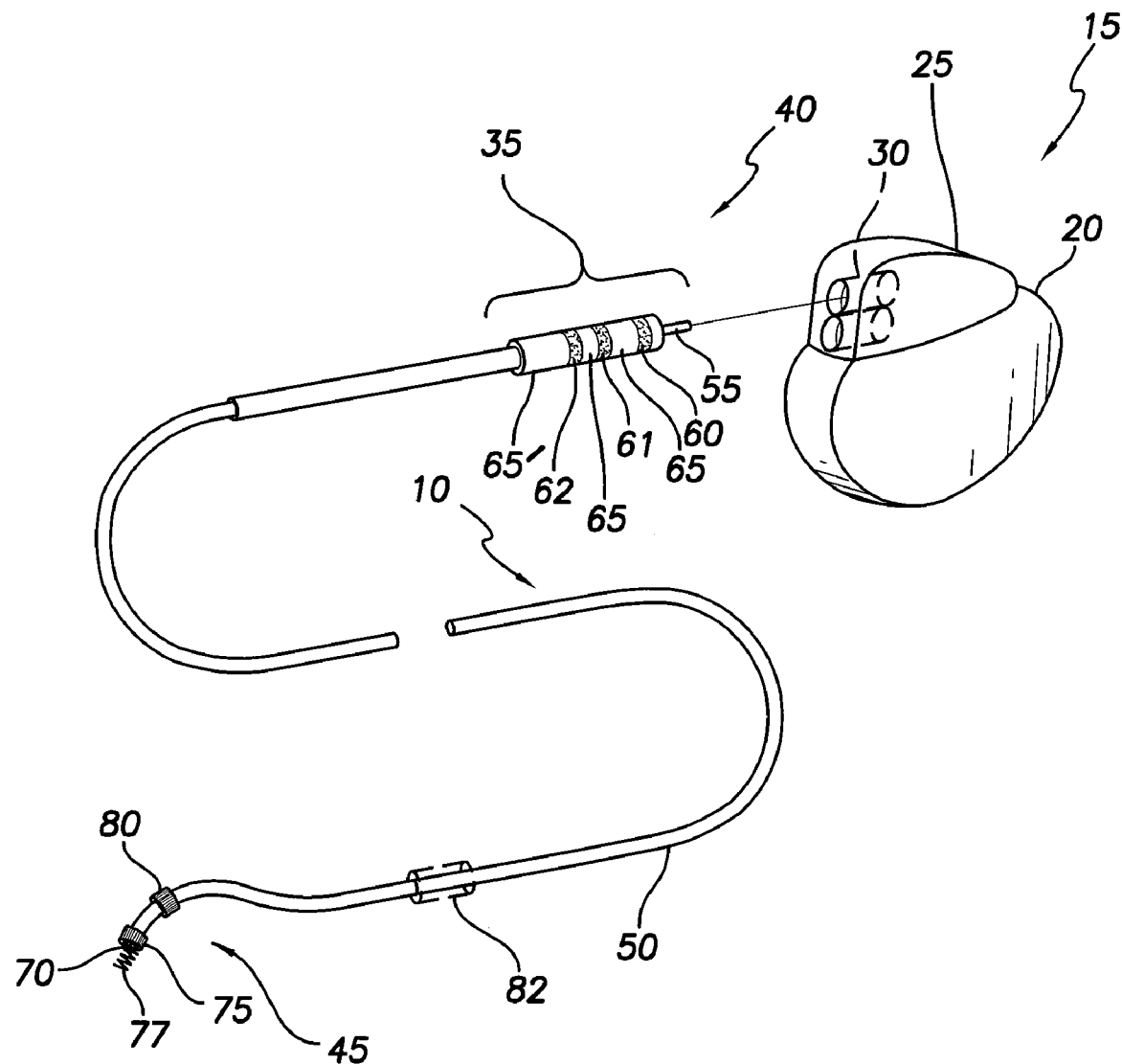
FIG. 1 is an isometric view of an implantable medical lead and a pulse generator for connection thereto.

For a general discussion of an embodiment of a lead 10 employing the connector pin retention assembly 120, reference is made to FIG. 1, which is an isometric view of the implantable medical lead 10 and a pulse generator 15 for connection thereto. The pulse generator 15 may be a pacemaker, defibrillator, ICD or neurostimulator. As indicated in FIG. 1, the pulse generator 15 may include a can 20, which may house the electrical components of the pulse generator 15, and a header 25. The header may be mounted on the can 20 and may be configured to receive a lead connector end 35 in a lead receiving receptacle 30.

As shown in FIG. 1, in one embodiment, the lead 10 may include a proximal end 40, a distal end 45 and a tubular body 50 extending between the proximal and distal ends. In some embodiments, the lead may be a 6 French, model 1688T lead, as manufactured by St. Jude Medical of St. Paul, Minn. In other embodiments, the lead may be a 6 French model 1346T lead, as manufactured by St. Jude Medical of St. Paul, Minn. In other embodiments, the lead 10 may be of other sizes and models. The lead 10 may be configured for a variety of uses. For example, the lead 10 may be a RA lead, RV lead, LV Brady lead, RV Tachy lead, intrapericardial lead, etc.

As indicated in FIG. 1, the proximal end 40 may include a lead connector end 35 including a pin contact 55, a first ring contact 60, a second ring contact 61, a third ring contact 62, and sets of spaced-apart sealing regions or seals 65. In some embodiments, the lead connector end 35 may include the same or different seals and may include a greater or lesser number of contacts. The lead connector end 35 may be received in a lead receiving receptacle 30 of the pulse generator 15 such that the seals 65 prevent the ingress of bodily fluids into the respective receptacle 30 and the contacts 55, 60, 61, 62 electrically contact corresponding electrical terminals within the respective receptacle 30.

As illustrated in FIG. 1, in one embodiment, the lead distal end 45 may include a distal tip 70, a tip electrode 75 and a ring electrode 80. In some embodiments, the lead body 50 is configured to facilitate passive fixation and/or the lead distal end 45 includes features that facilitate passive fixation. In such passive fixation embodiments, the tip electrode 75 may be in the form of a ring or domed cap and may form the distal tip 70 of the lead body 50. In some embodiments, the tip electrode 75 may be in the form of a helical anchor 77 that is extendable from within the distal tip 70 for active fixation and serving as a tip electrode 77.

As shown in FIG. 1, in some embodiments, the distal end 45 may include a defibrillation coil 82 about the outer circumference of the lead body 50. The defibrillation coil 82 may be located proximal of the ring electrode 70.

The ring electrode 80 may extend about the outer circumference of the lead body 50, proximal of the distal tip 70. In other embodiments, the distal end 45 may include a greater or lesser number of electrodes 75, 80 in different or similar configurations.

Figure 2:
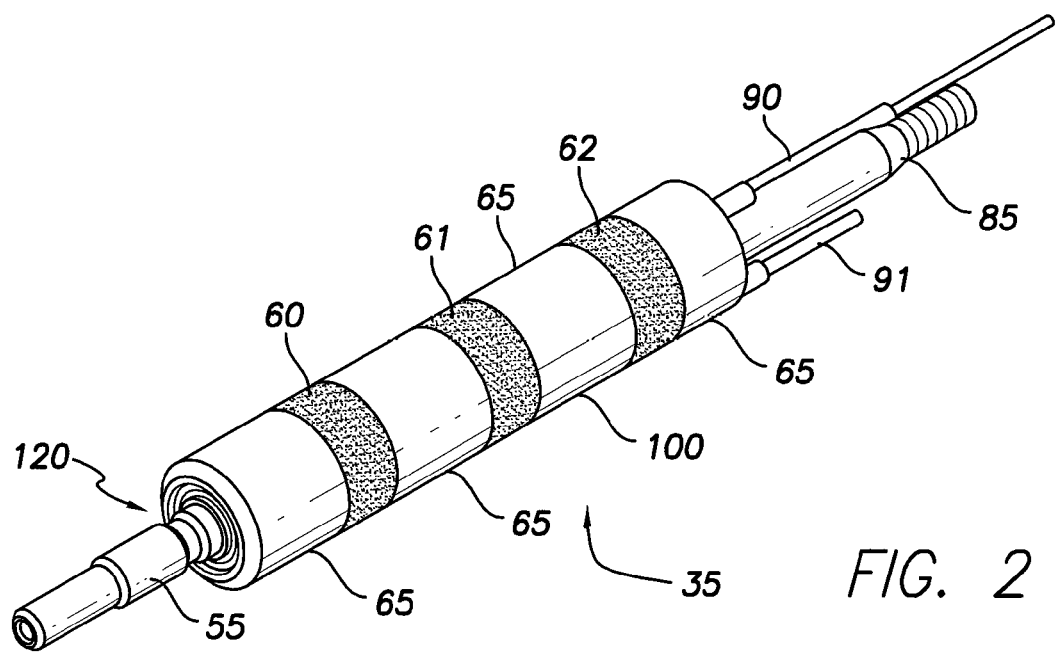
FIG. 2 is an isometric view of an embodiment of the lead connector end depicted in FIG. 1.
Figure 3:
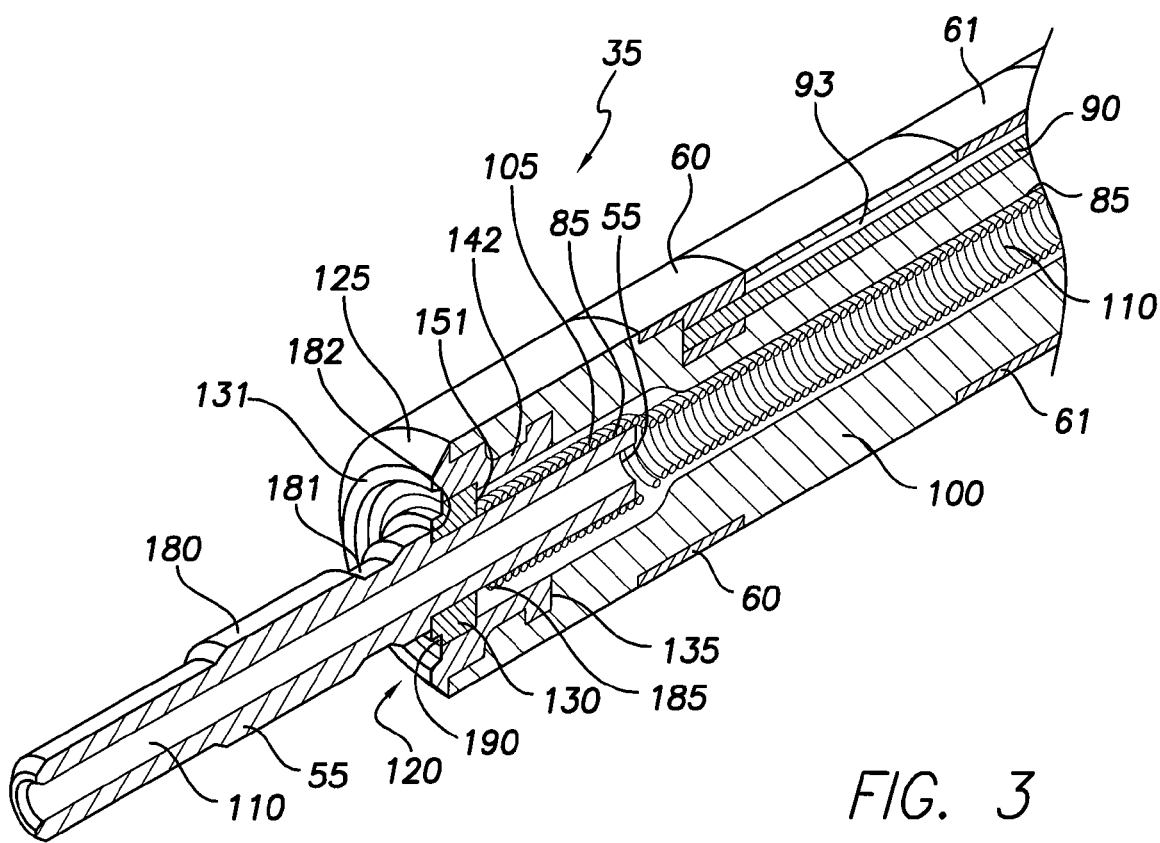
FIG. 3 is an isometric longitudinal cross-section of the lead connector end of FIG. 2.

As can be understood from FIG. 1 and also FIGS. 2 and 3, which are, respectively, an isometric and an isometric longitudinal cross-section of the lead connector end 35, in one embodiment, the tip electrode 75 may be in electrical communication with the pin contact 55 via a first electrical conductor 85, and the ring electrode 80 may be in electrical communication with the first ring contact 60 via a second electrical conductor 90. In some embodiments, the defibrillation coil 82 may be in electrical communication with the second ring contact 61 via a third electrical conductor 91. In yet other embodiments, other lead components (e.g., additional ring electrodes, various types of sensors, etc.) (not shown) mounted on the lead body distal region 45 or other locations on the lead body 50 may be in electrical communication with a third ring contact 62 similar to the second ring contact 61 via a fourth electrical conductor 92. Depending on the embodiment, any one or more of the conductors 85, 90, 91, 92 may be a multi-strand or multi-filar cable or a single solid wire conductor run singly or grouped, for example in a pair. In one embodiment, as indicated in FIG. 3, the first conductor 85 may be a helical coil conductor 85 formed of multiple filars helically wound into a helical coil, and the other conductors 90-92 may be solid or multi-filar cable conductors 90-92 extending through wall lumens 93 in the lead body 50.

As can be understood from FIG. 3, in one embodiment, the lead connector end 35 includes a body 100 in which the ring contacts 60-62 are imbedded and through which the contact pin 55 and conductors 85, 90-92 extend. In one embodiment, the body 100 is formed of a polymer material, such as, for example, polyetheretherketone ("PEEK"), tecothane, etc.

As shown in FIG. 3, the contact pin 55 is mechanically and electrically connected to a proximal end of the helical coil conductor 85. The mechanical and electrical connection between the distal end of the contact pin 55 and the proximal end of the helical coil conductor 85 may be achieved via such methods as welding, brazing and mechanical arrangements. For example, with respect to mechanical arrangements, as illustrated in FIG. 3, the distal end of the contact pin 55 may be received within the proximal end of the helical coil conductor 85, and a mechanical crimp sleeve 105 may be crimped about the proximal end of the helical coil conductor 85 to mechanically and electrically connect the helical coil conductor 85 to the contact pin 55. The contact pin 55 and the helical coil conductor 85 both include lumens and are both connected to each other such that their respective lumens combine to form a central lumen 110 that extends distally through the lead connector end 35 and lead body 50 via the contact pin 55 and the helical coil conductor 85. The central lumen 110 may receive guidewires and stylets there through during delivery of the lead distal end to the implantation site.

As indicated in FIG. 3, the contact pin 55 may be retained within the body 100 of the lead connector end 35 via a contact pin retainer assembly 120. In some embodiments, the assembly 120 may be configured to not only retain the contact pin 55, but allow the contact pin 55 and helical coil conductor 85 to rotate relative to the lead connector end body 100 and the lead body 50. In other embodiments, the assembly 120 may be configured to simply retain the contact pin 55 and not allow the contact pin 55 to rotate relative to the lead connector end body 100 and the lead body 50. In either case, the retainer assembly 120 may include a collar 125, which may be imbedded or otherwise received in the lead connector end body 100, and a cap 130, which may be received within the collar 125.

Figure 4:
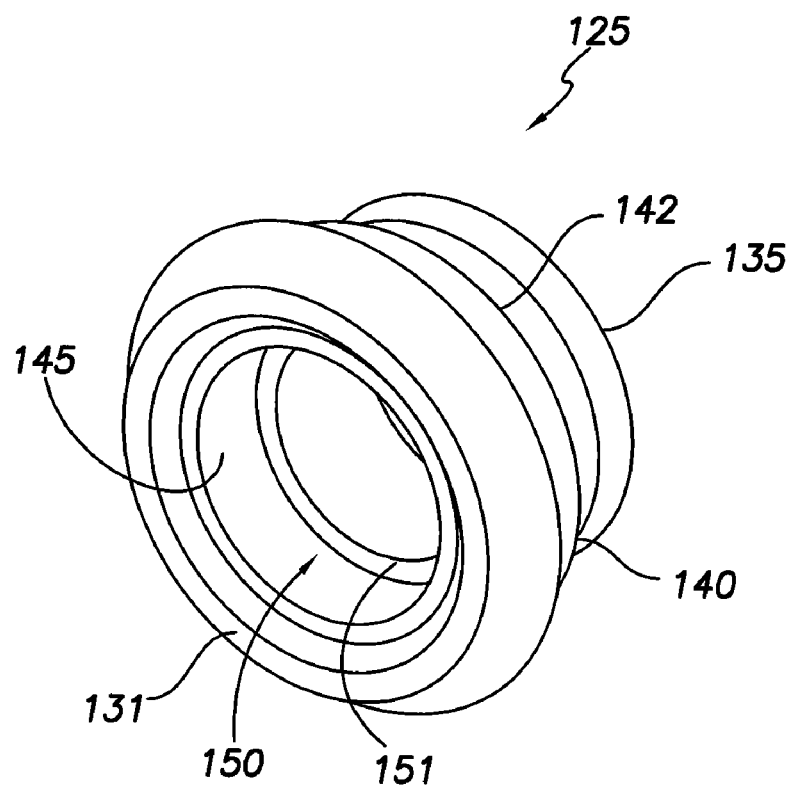
FIG. 4 is an isometric view of the collar depicted in FIG. 3.

As can be understood from FIG. 4, which is an isometric view of the collar 125 depicted in FIG. 3, the collar 125 may include a proximal face 131, a distal face 135, an outer circumferential surface 140, and an inner circumferential surface 145. As can be understood from FIGS. 3 and 4, the proximal face 131 may be chamfered or tapered to provide the lead connector end 35 with a tapered or chamfered end to facilitate the proximal end of the lead connector end 35 being received in the pulse generator. The outer circumferential surface 140 may diametrically vary to define a grove 142 or other features that facilitate the collar 125 being securing imbedded in the material of the body 100. The inner circumferential surface 145, which defines an opening 150 that extends through the collar 125 to receive the cap 130, may also diametrically vary to define a rim 151 or other feature that assists in distally-proximally positioning the cap 130 when received in the opening 150.

Figure 5:
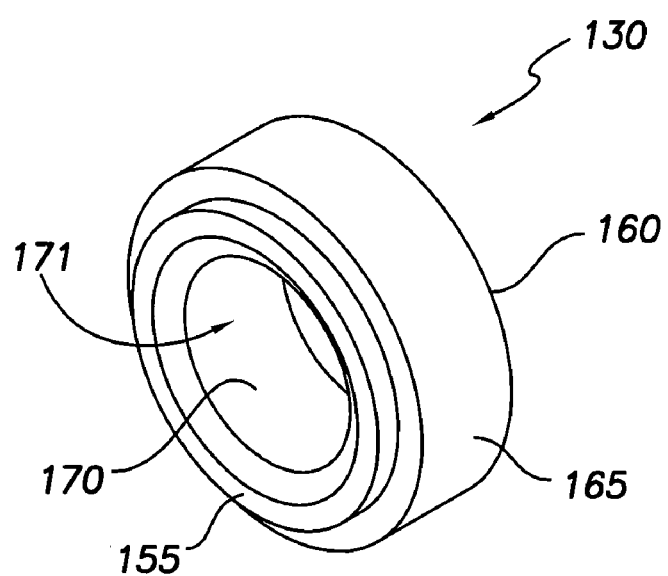
FIG. 5 is an isometric view of the cap depicted in FIG. 3.

As shown in FIG. 5, which is an isometric view of the cap 130 depicted in FIG. 3, the cap 130 may include a proximal face 155, a distal face 160, an outer circumferential surface 165, and an inner circumferential surface 170, which defines an opening 171. As can be understood from FIGS. 3-5, the cap 130 may be received in the collar opening 150 such that the cap outer circumferential surface 165 is matingly received by the collar inner circumferential surface 145, the cap distal face 160 abutting against the collar rim 151 to prevent the cap 130 from moving any more distal in the collar opening 150.

As shown in FIG. 3, the outer circumferential surface 180 of the contact pin 55 may vary to define such features as a groove 181 and a ridge 182. The groove 181 may mate with a retaining feature such as, for example, a set screw when the contact pin 55 is received in the pulse generator. The contact pin 55 is received in the cap opening 171 such that a portion of the outer circumferential surface 180 distal of the ridge 182 is matingly received by the cap inner circumferential surface 170, the contact pin ridge 182 abutting against the cap proximal face 155 to prevent the contact pin 55 from moving any more distal through the cap hole 171. The proximal edge of the crimp sleeve 105, which extends about the helical coil conductor 85 that extends about the distal portion of the contact pin outer circumferential surface 180, exceeds the diameter of the cap hole 171, thereby preventing the contact pin 55 from displacing proximally within the cap hole 171.

In some embodiments, the portion of the outer circumferential surface 180 of the contact pin 55 distal the contact pin ridge 182 is matingly received by the cap inner circumferential surface 170 such that a bearing arrangement 185 is formed by the two surfaces, thereby allowing the contact pin 55 to rotate within the cap hole 171 and relative to the cap 130 and the rest of the lead connector end 35, which allows the contact pin 55 to be used to rotate the helical coil conductor 85 relative to the lead body 50.

In one embodiment, portions of the cap outer circumferential surface 165 are welded to portions of the collar inner circumferential surface 145 to form a welded seam or region 190 securing the cap 130 within the collar 125. In one embodiment, the welding may be performed via laser or other welding methods, including chemical welding, depending on the materials forming the cap and collar. In some embodiments, brazing or other joining methods are substituted for welding.

In some embodiments, the collar 125 and cap 130 are formed from a metal material such as, for example, MP35N, stainless steel, tantalum, etc. In some embodiments, the collar 125 and cap 130 are formed from a ceramic, polymer or other appropriate material.

As mentioned immediately above, a bearing arrangement may exist between the cap 130 and contact pin 55 such that the pin 55 may rotate relative to the cap 130 and the rest of the lead connector end 35. However, in some embodiments, the contact pin 55 may be fixed relative to or even integrally formed with the cap 130 such that the contact pin 55 does not rotate relative to the cap 130. In some such embodiments, the cap 130 may be fixed relative to the collar 125 such that the cap 130 does not rotate relative to the cap 130 and, as a result, the contact pin 55 will not be rotate relative to the rest of the assembly 120 or the rest of the lead connector end 35.

In other embodiments where the contact pin 55 is fixed to or integrally formed with the cap 130 such that the contact pin 55 will not rotate relative to the cap 130, the cap 130 may be rotatably attached to the collar 125 such that a bearing arrangement may exist between the cap 130 and the collar 130. As a result, the contact pin 55 and cap 130 may rotate as a unit relative to the collar 125 and the rest of the assembly 120 or the rest of the lead connector end 35.

Depending on which components (i.e., contact pin 55, cap 130 and collar 125) are rotatable relative to each other, the components 55, 130, 125 may be formed from a variety of materials. For example, if the pin 55 is rotatably coupled to the cap 130 and the cap 130 is non-rotatably coupled to the collar 125, the cap 130 may be formed from a non-metallic material and the collar 125 may be formed from a metallic or non-metallic material. As another example, if the pin 55 is non-rotatably coupled to the cap 130 and the cap 130 is rotatably coupled to the collar 125, the cap 130 may be formed from a metallic material and the collar 125 may be formed from a non-metallic material. As yet another example, if the pin 55 is non-rotatably coupled to the cap 130 and the cap 130 is rotatably coupled to the collar 125, the cap 130 may be formed from a non-metallic material and the collar 125 may be formed from a metallic or non-metallic material. Other combinations may be available as long as adjacent rotating parts (e.g., the pin 55 rotatable relative to the cap 130 or the cap 130 rotatable relative to the collar 125) are not both formed of a metallic material, thereby avoiding the possibility of electrical chatter resulting from adjacent metallic surfaces rotating against each other. Where the pin 55, cap 130 and collar 125 are all coupled together in a non-rotatable fashion, the cap 130 and collar 125 may be both formed of metallic material, both formed of non-metallic material, or formed of a combination of metallic and non-metallic material.

In one embodiment, the contact pin 55, retainer assembly 120, crimp sleeve 105 and helical coil conductor 85 are assembled together within the lead connector end body 100 as follows. The lead connector end body 100 is provided, wherein the body 100 has imbedded therein the collar 125, the contact rings 60-61 and contact rings' corresponding conductors 90-92. The distal end of the contact pin 55 is inserted through the cap hole 170 until the contact pin ridge 182 abuts the cap proximal face 155. The distal end of the contact pin 55 is inserted into the proximal end of the lumen of the helical coil conductor 85, and the crimp sleeve 105 is placed about the helical coil conductor 85 where the conductor 85 extends over the distal end of the contact pin 55. The crimp sleeve 105 is crimped down on the conductor 85, thereby securing the conductor 85 to the contact pin 55. As can be understood from FIG. 3, the contact pin ridge 183 and proximal end of the crimp sleeve 105 now respectively prevent the cap 130 from proximally and distally displacing along the contact pin 55. However, the bearing arrangement 185 between the cap 130 and pin 55 allows the pin 55 to rotate within the cap hole 170. The assembly formed by the conductor pin 55, conductor 85, crimp sleeve 105 and cap 130 is inserted as a whole into the body 100 by routing the distal end of the conductor 85 into the collar hole 150 and continuing to feed this assembly into the collar hole 150 until the cap 130 is received in the collar hole 150, the collar rim 151 and cap distal face 160 abutting and arresting further distal displacement of the assembly through the collar hole 150. Portions of the cap outer circumferential surface 165 are then joined, for example, via welding or other appropriate methods, to portions of the collar inner circumferential surface 145, thereby securing the assembly formed by the conductor pin 55, conductor 85, crimp sleeve 105 and cap 130 within the connector body 100 such that the pin 55 and conductor 85 may be rotated within the connector body 100, but not displace distally or proximally within the connector body 100.

Of course, as discussed above, in some embodiments, the components of the assembly 120 may be coupled together and formed of materials that allow the pin 55 and cap 130 to rotate together as a unit relative to the collar 125 or, alternatively, the pin 55, cap 130 and collar 125 are coupled together such that the pin 55 does not rotate relative to the cap 130, collar 125 or the rest of the connector end 35.

Figure 6:
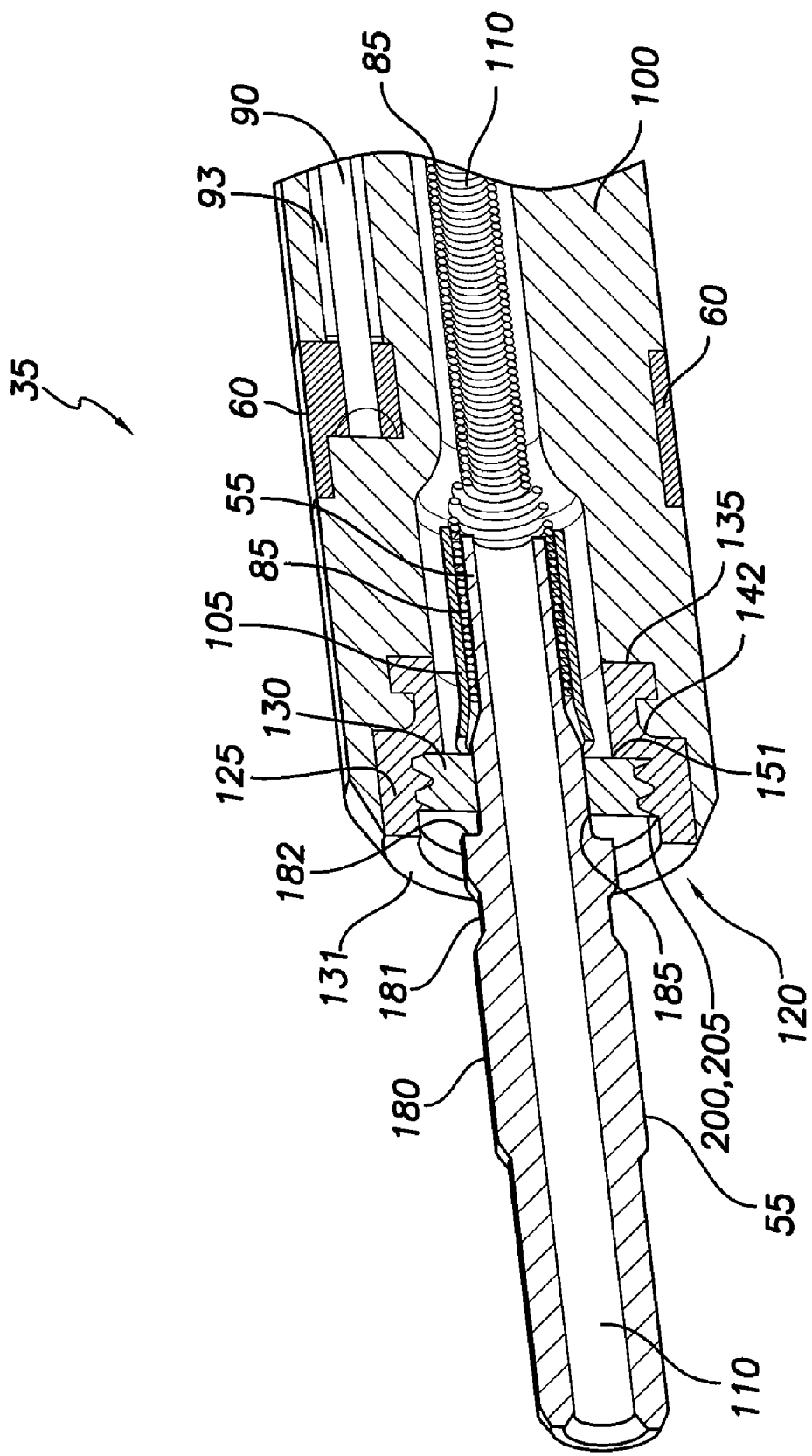
FIG. 6 is the same isometric view as depicted in FIG. 3, except of an embodiment of the contact pin retainer assembly employing a thread arrangement between the collar and cap.
Figure 7:
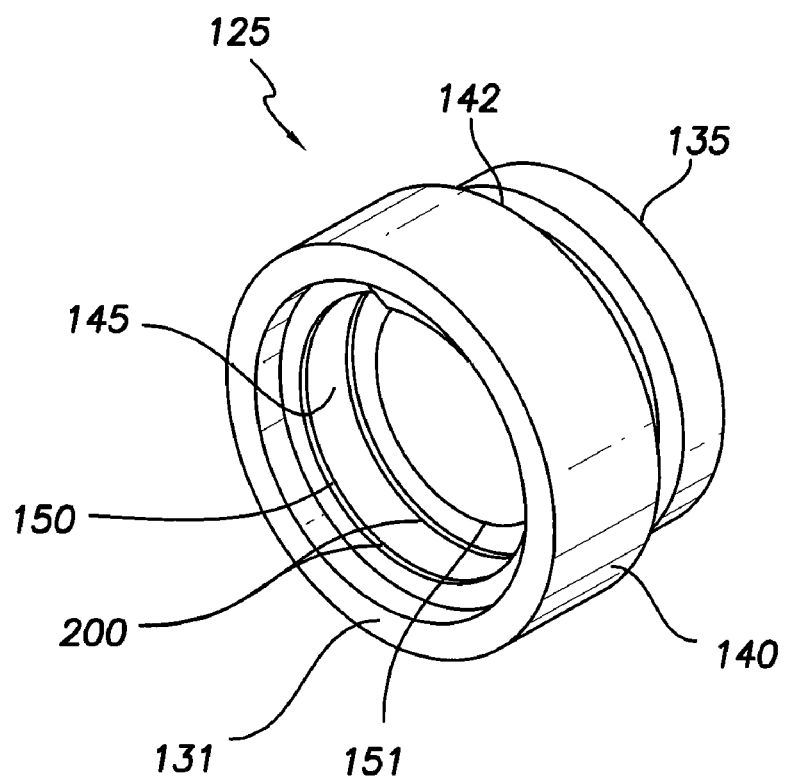
FIG. 7 is the same view as FIG. 4, except of the threaded collar of FIG. 6.
Figure 8:
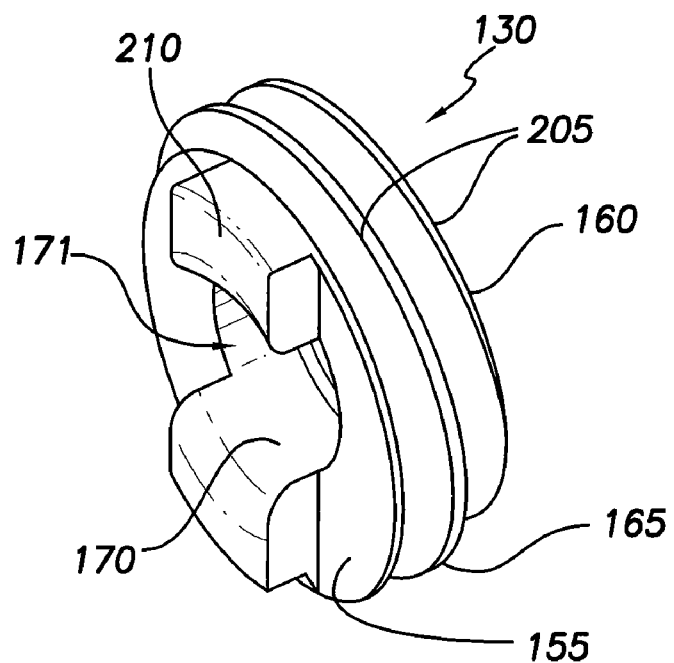
FIG. 8 is the same view as FIG. 5, except of the threaded cap of FIG. 6.

In some embodiments, the contact pin retainer assembly 120 will have other configurations whereby the cap 130 is secured to the collar 125. For example, as indicated in FIGS. 6-8, which are, respectively, views similar to those of FIGS. 3-5, the inner circumferential surface 145 of the collar 125 includes threads 200 defined therein, and the outer circumferential surface 165 of the cap 130 includes threads 205 defined therein. Thus, as can be understood from FIGS. 6-8, once the assembly formed by the conductor pin 55, conductor 85, crimp sleeve 105 and cap 130 is assembled as described above with respect to FIGS. 3-5 and then routed through the collar hole 150 and lead connector end body 100 as described above with respect to FIGS. 3-5, the cap 130 may be threaded into the collar 125 via the threads 200, 205 until the cap 130 is fully threaded into the collar 125, the cap distal face 160 abutting against the collar rim 151. Through the threaded arrangement depicted in FIGS. 6-8, the assembly formed by the conductor pin 55, conductor 85, crimp sleeve 105 and cap 130 may be secured within the connector body 100 such that the pin 55 and conductor 85 may be rotated within the connector body 100, but not displace distally or proximally within the connector body 100.

Of course, as discussed above, in some embodiments, the components of the assembly 120 may be coupled together and formed of materials that allow the pin 55 and cap 130 to rotate together as a unit relative to the collar 125 or, alternatively, the pin 55, cap 130 and collar 125 are coupled together such that the pin 55 does not rotate relative to the cap 130, collar 125 or the rest of the connector end 35.

In one embodiment, the thread 200, 205 may be 2-56 thread. In other embodiments, the thread 200, 205 may be of other types.

Figure 9:
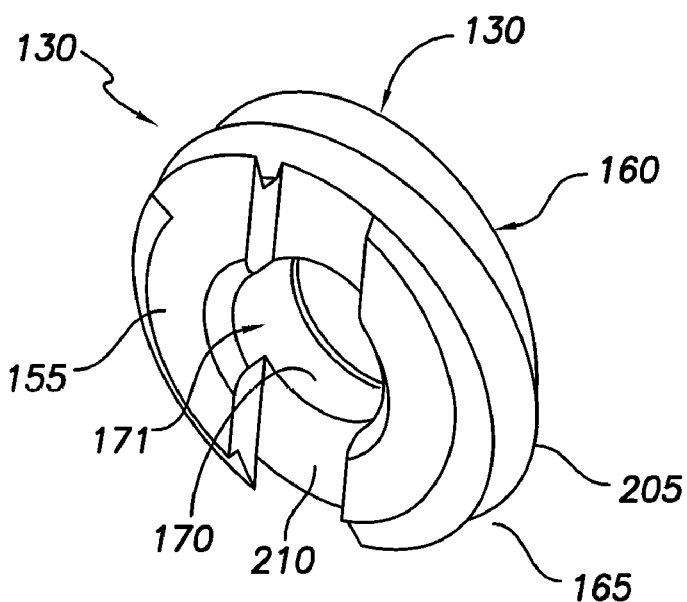
FIGS. 9-11 are, respectively, proximal isometric, side isometric and distal isometric views of the threaded cap of FIG. 6.
Figure 10:
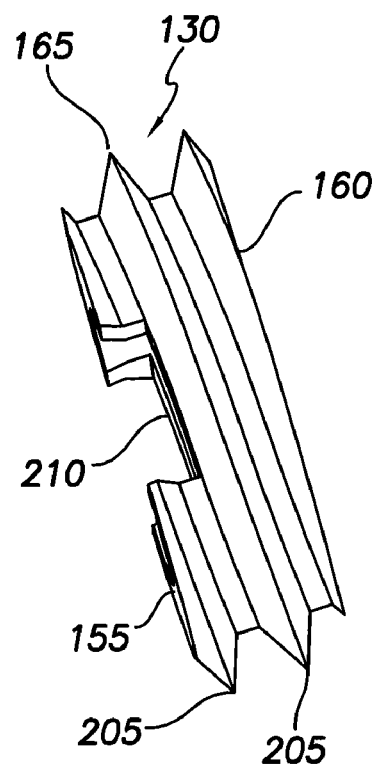
Figure 11:
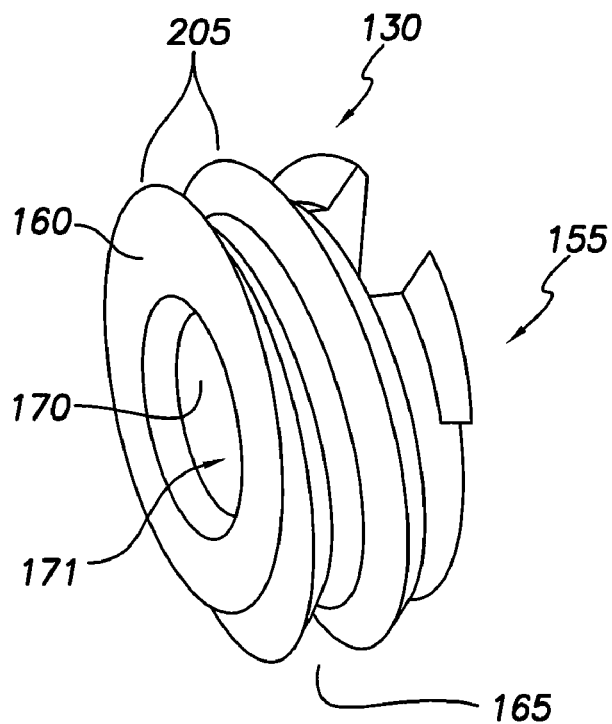

As indicated in FIG. 8, in some embodiments, the cap proximal face 155 may include a ridge or male feature 210 that projects proximally from the cap proximal face 155 such that the feature 210 may be received in a female type screw driver head or wrench attachment. In a similar, but generally opposite fashion, as depicted in FIGS. 9-10, which are, respectively, proximal, side and distal isometric view of the cap 130, the cap proximal face 155 may include a slot or female feature 210 that is recessed distally into the cap proximal face 155 such that the feature 210 may receive a male type screw driver head or wrench attachment.

Figure 12:
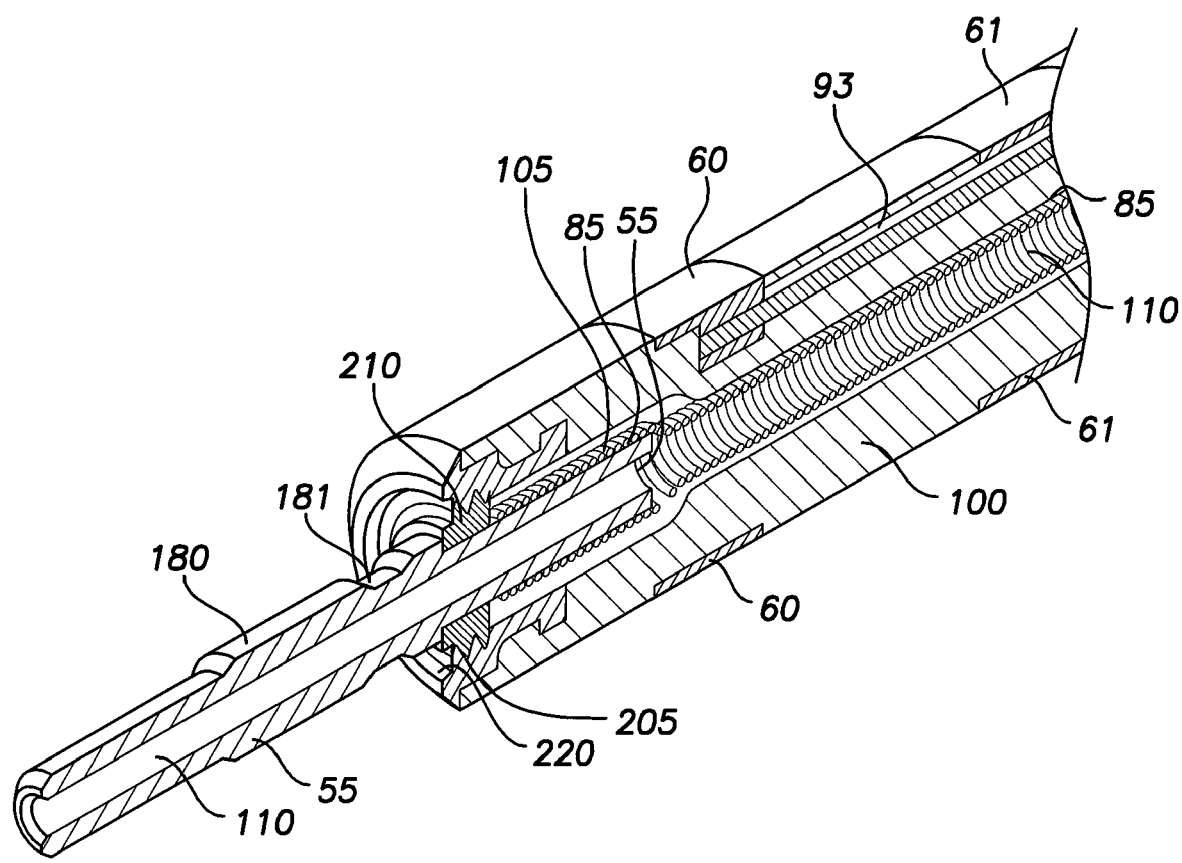
FIG. 12 is the same isometric view as depicted in FIG. 6, except of an embodiment of the contact pin retainer assembly that does not employ a collar, but instead relies on the threads to self-tap the cap into the material forming the lead connector end body.

As can be understood from FIGS. 6-8, in one embodiment, the contact pin retainer assembly 120 may include a collar 125, which in a manner similar to the collar 120 discussed with respect to FIGS. 3-5, may be an imbedded part of the lead connector end body 100. However, as depicted in FIG. 12, which is a view similar to that of FIGS. 3 and 6, a collar 125 may not be part of the contact pin retainer assembly 120. Instead, the assembly 120 may employ a cap 130 having self-tapping threads 205 defined in its outer circumferential surface 165, the self-tapping threads 205 threading themselves into the material of the lead connector end body 100 that forms an inner circumferential surface 220 of the proximal portion of the lead connector end body 100.

In some embodiments, the contact pin retainer assembly 120 will have yet other configurations whereby the cap 130 is secured to the collar 125. For example, as indicated in FIGS. 13, 16 and 14, which are, respectively, views similar to those of FIGS. 3-5, the collar 125 and cap 130 may be configured such that they connect securely together via an interference or biased type fit.

Figure 13:
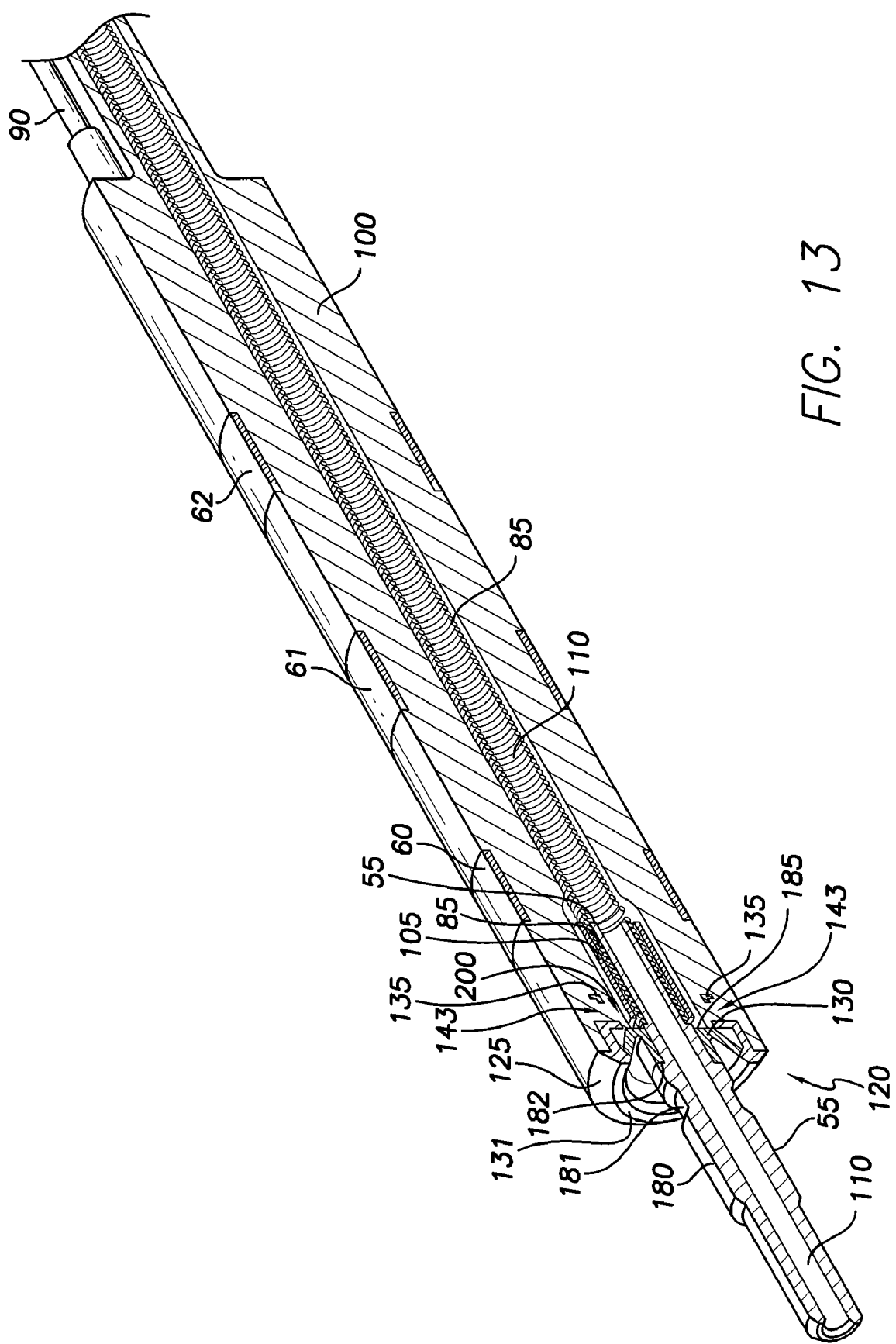
FIG. 13 is the same isometric view as depicted in FIG. 3, except of an embodiment of the contact pin retainer assembly employing an interference or biased fit arrangement between the collar and cap.
Figure 14:
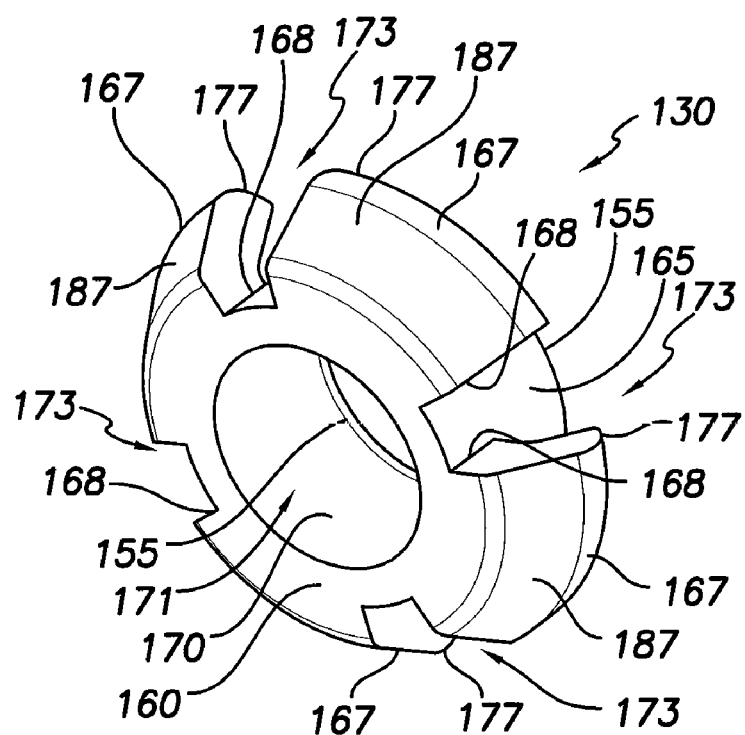
FIGS. 14 and 15 are respective distal and proximal isometric views of a first embodiment of the cap 130 depicted in FIG. 13

In a manner similar to the above-discussed embodiments and as can be understood from FIG. 13, the contact pin 55 may be retained within the body 100 of the lead connector end 35 via a contact pin retainer assembly 120. The assembly 120 may be configured to not only retain the contact pin 55, but allow the contact pin 55 and helical coil conductor 85 to rotate relative to the lead connector end body 100 and the lead body 50. The retainer assembly 120 may include a collar 125, which may be imbedded or otherwise received in the lead connector end body 100, and a cap 130, which may be received within the collar 125.

Figure 16:
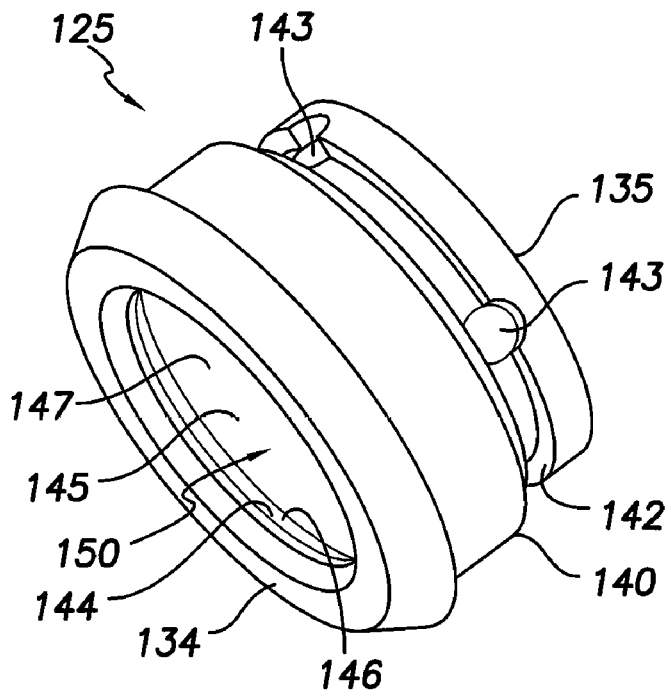
FIGS. 16 and 17 are respectively proximal and distal isometric views of the collar 125 depicted in FIG. 13.
Figure 17:
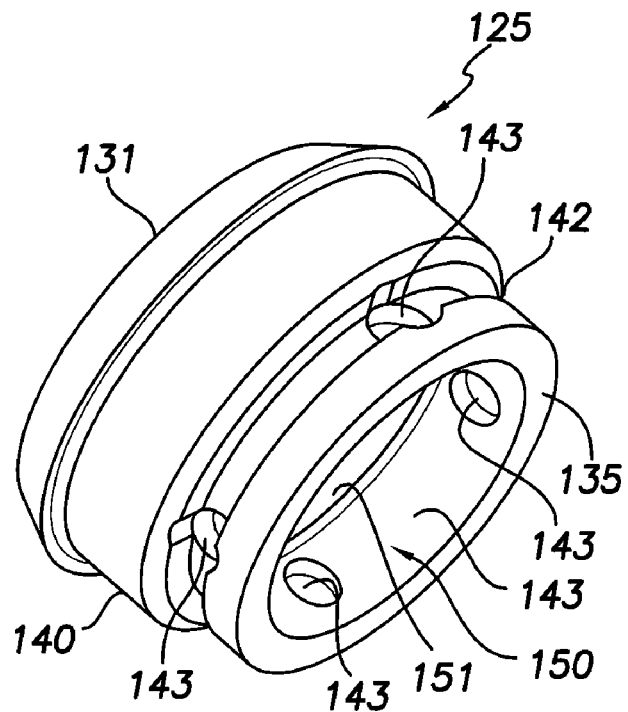
Figure 18:
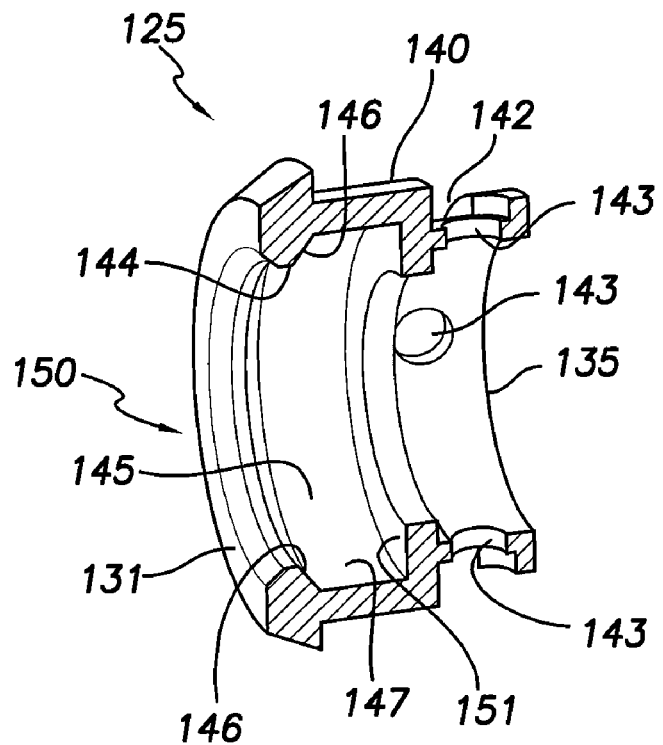
FIGS. 18 and 19 are respectively proximal and distal isometric longitudinal cross sections of the collar.
Figure 19:
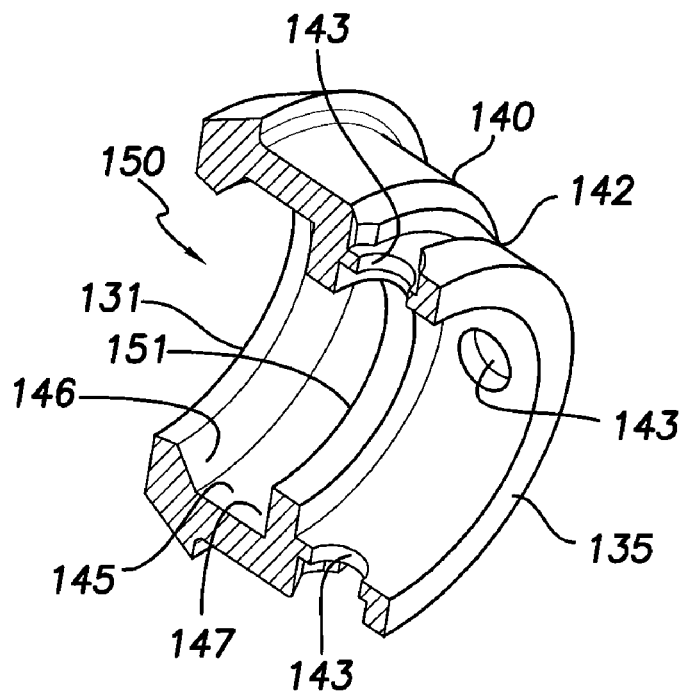

As can be understood from FIGS. 16-17, which are respectively proximal and distal isometric views of the collar 125 depicted in FIG. 13, and FIGS. 18-19, which are respectively proximal and distal isometric longitudinal cross sections of the collar 125, the collar 125 may include a proximal face 131, a distal face 135, an outer circumferential surface 140, and an inner circumferential surface 145. As can be understood from FIGS. 13 and 16-17, the proximal face 131 may be chamfered or tapered to provide the lead connector end 35 with a tapered or chamfered end to facilitate the proximal end of the lead connector end 35 being received in the pulse generator. The outer circumferential surface 140 may diametrically vary to define a grove 142 or other features that facilitate the collar 125 being securely imbedded in the material of the body 100. In some embodiments, as depicted in FIGS. 16-19, openings 143 may be defined in the groove 142 to extend through the wall of the collar 125 from the outer circumferential surface 140 to the inner circumferential surface 145. As indicated in FIG. 13, the material of the body 100 may fill the openings 143 when the collar 125 is imbedded in the material of the body 100.

The inner circumferential surface 145, which defines an opening 150 that extends through the collar 125 to receive the cap 130, may also diametrically vary to define a rim 151 or other feature that assists in distally-proximally positioning the cap 130 when received in the opening 150. In some embodiments, as depicted in FIGS. 16-19, a proximal lip 144 may be defined in the inner circumferential surface 145 proximally offset from the rim 150. The lip 144 may have a sloped distal face 146, while the proximal face of the rim 150 may be generally perpendicular to the longitudinal axis of the collar 125. A circumferentially extending portion 147 of the inner circumferential surface 145 may be defined between the lip 144 and the rim 150. As indicated in FIG. 13, winged portions 167 of the cap 130, which are discussed below, are received in the circumferentially extending portion or space 147 when the cap 130 is secured in the collar 125 via the resulting bias or interference type fit created between the winged portions 167 and the lip 144.

Figure 15:
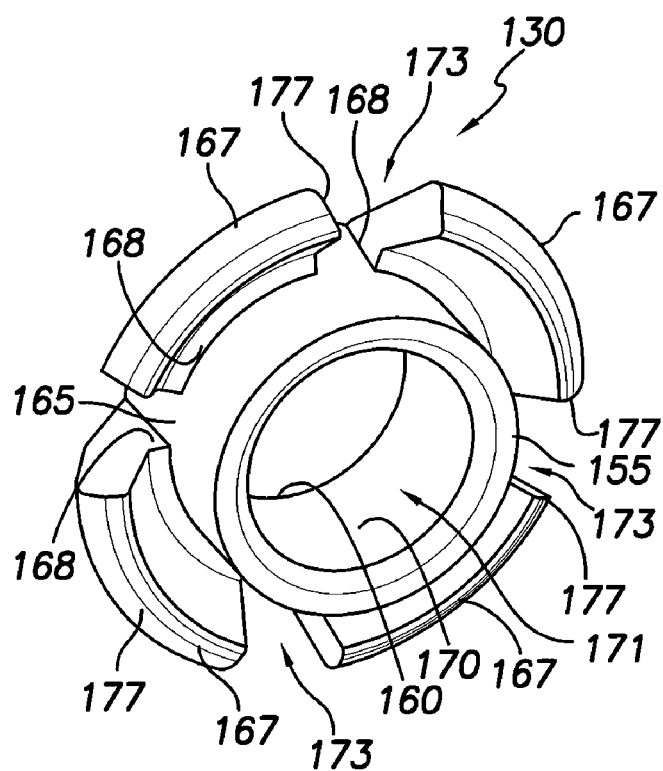

As shown in FIGS. 14 and 15, which are respective distal and proximal isometric views of a first embodiment of the cap 130 depicted in FIG. 13, the cap 130 may include a proximal face 155, a distal face 160, an outer circumferential surface 165, multiple wings 167, and an inner circumferential surface 170 that defines an opening 171. In one embodiment, each wing 167 extends both radially outward and proximally from the outer circumferential surface 165 beginning at or near the distal face 160. Thus, as can be understood from FIGS. 13-15, each wing 167 includes a base 168 that is joined to the outer circumferential surface 165 near the distal face 160, and each wing 167 includes a proximal tip or free end 177 that is both radially outwardly spaced from the outer circumferential surface 165 and proximally offset from the its base 168.

Figure 20:
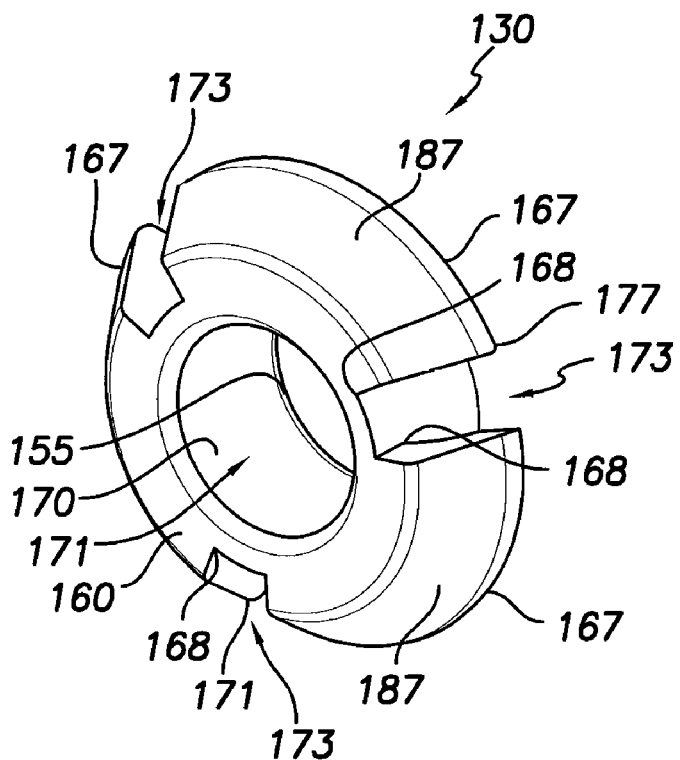
FIGS. 20 and 21 are the same respective views of the cap as depicted in FIGS. 14 and 15, except of another embodiment.
Figure 21:
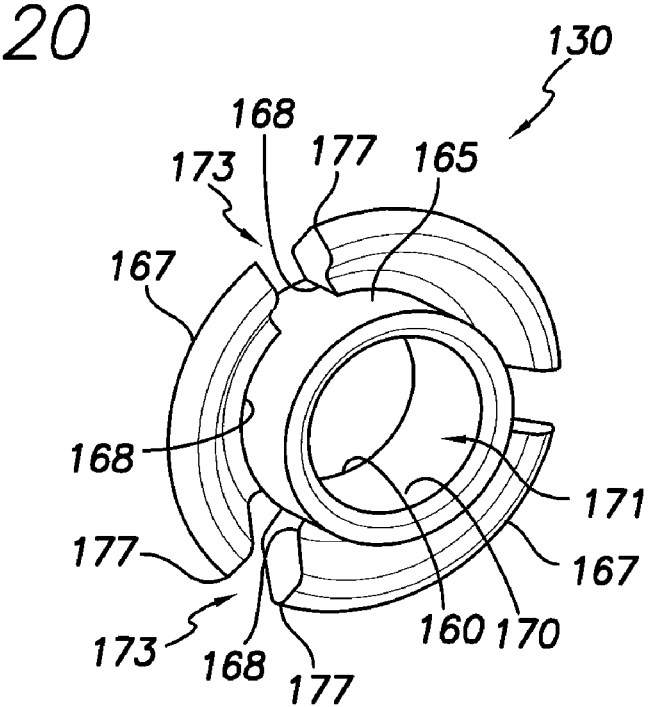

As can be understood from FIGS. 14 and 15, in one embodiment, the cap 130 may have four wings 167 evenly radially spaced about the outer circumferential surface 165 of the cap 130 and spaced apart from each other via gaps or spaces 173 between the sides of the wings 167. As can be understood from FIGS. 20 and 21, which are the same respective views as FIGS. 14 and 15, but of another embodiment, the cap 130 may have three wings 167 evenly radially spaced about the outer circumferential surface 165 of the cap 130 and spaced apart from each other via gaps or spaces 173 between the sides of the wings 167. In other embodiments, the cap 130 may have other numbers of wings 167, for example, one, two, three, five, six, or more wings 167.

As can be understood from FIG. 13, the cap 130 may be received in the collar opening 150 such that the wings 167 are matingly received by the circumferentially extending portion 147 of the collar inner circumferential surface 145, the cap distal face 160 abutting against the collar rim 151 to prevent the cap 130 from moving any more distal in the collar opening 150, and the free ends 177 of each wing 167 abutting against the inclined distal face 146 of the collar 125.

As can be understood from FIGS. 13-15 and 20-21, each wing 167 may include an inclined distal face 187. As each wing free end 177 is radially offset from the cap outer circumferential surface 165, when the cap 130 is distally inserted distal end first into the collar opening 150, each wing inclined distal face 187 abuts against the proximal edge of the collar proximal face 131 to deflect radially inward until the each wing free end 177 clears the collar proximal lip 144 as the wings 167 enter the space 147 defined between the surfaces 146 and 151. Once the wing free ends 177 clear the collar proximal lip 144, the wings 167 bias radially outward or otherwise self expand radially outward until the wing free ends 177 abut against the collar inclined distal face 146. Such radial expansion of the wing free ends 177 sufficiently increases the overall cap diameter to prevent the proximal withdrawal of the cap 130 from the collar hole 150, thus allowing the cap 130 to retain the pin 55 within the lead connector end 35. The resulting interaction between the wing free ends 177 and the lip 144 of the collar 125 may be considered to be an interference fit connection arrangement. In some embodiments, the wing fee ends 177 may bias into expanded engagement with the lip 144 with sufficient force to cause an audible snap sound, and the interference fit connection arrangement may be classified a snap fit connection arrangement.

As shown in FIG. 13 as previously explained with respect to FIG. 3, the outer circumferential surface 180 of the contact pin 55 may vary to define such features as a groove 181 and a ridge 182. The groove 181 may mate with a retaining feature such as, for example, a set screw when the contact pin 55 is received in the pulse generator. The contact pin 55 is received in the cap opening 171 such that a portion of the outer circumferential surface 180 distal of the ridge 182 is matingly received by the cap inner circumferential surface 170, the contact pin ridge 182 abutting against the cap proximal face 155 to prevent the contact pin 55 from moving any more distal through the cap hole 171. The proximal edge of the crimp sleeve 105, which extends about the helical coil conductor 85 that extends about the distal portion of the contact pin outer circumferential surface 180, exceeds the diameter of the cap hole 171, thereby preventing the contact pin 55 from displacing proximally within the cap hole 171.

In some embodiments, the portion of the outer circumferential surface 180 of the contact pin 55 distal the contact pin ridge 182 is matingly received by the cap inner circumferential surface 170 such that a bearing arrangement 185 is formed by the two surfaces, thereby allowing the contact pin 55 to rotate within the cap hole 171 and relative to the cap 130 and the rest of the lead connector end 35, which allows the contact pin 55 to be used to rotate the helical coil conductor 85 relative to the lead body 50.

Thus, as can be understood from FIGS. 13-21, once the assembly formed by the conductor pin 55, conductor 85, crimp sleeve 105 and cap 130 is assembled as described above with respect to FIGS. 3-5 and then routed through the collar hole 150 and lead connector end body 100 as described above with respect to FIGS. 3-5, the cap 130 may be distally inserted into the collar opening 150 be until the cap wing free ends 177 fully clear the collar lip 144 and the wing free ends 177 bias into their radially expanded state. Through the interference or biased arrangement depicted in FIG. 13, the assembly formed by the conductor pin 55, conductor 85, crimp sleeve 105 and cap 130 may be secured within the connector body 100 such that the pin 55 and conductor 85 may be rotated within the connector body 100, but not displace distally or proximally within the connector body 100.

As with any of the above-discussed embodiments discussed with respect to FIGS. 3-12, in one or more of the embodiments discussed with respect to FIGS. 13-21, the collar 125 and cap 130 may be formed from a metal material such as, for example, MP35N, stainless steel, tantalum, etc. In some embodiments, the collar 125 and cap 130 may be formed from a ceramic, polymer or other appropriate material.

In one embodiment, the collar 125 is machined from a material, such as, for example, MP35N, that will facilitate high tolerance machining. As can be understood from FIG. 13, in one embodiment, a layer 200 of the body material 100, which may be Tecothane or another similar polymer, may extend between the collar 125 and the crimp sleeve 105 to electrically insulate the crimp sleeve 105, helical coil conductor 85 and pin 55 from the collar 125. In one embodiment, the cap 130 is formed of PEEK or a similar polymer.

In one embodiment, the collar 125 and cap 130 depicted in FIGS. 13-21 are advantageous for several reasons. First the collar and cap arrangement 120 maintain the pin 55 in the lead connector end 35 in a secure fashion. Secondly, the arrangement 120 does so in a manner that is easy to determine if the arrangement 120 is in fact securely holding the pin 55 or not.

As mentioned immediately above with respect to FIGS. 13-21, a bearing arrangement may exist between the cap 130 and contact pin 55 such that the pin 55 may rotate relative to the cap 130 and the rest of the lead connector end 35. However, in versions of the embodiments depicted in FIGS. 13-21, the contact pin 55 may be fixed relative to or even integrally formed with the cap 130 such that the contact pin 55 does not rotate relative to the cap 130. In some such embodiments, the cap 130 may be fixed relative to the collar 125 such that the cap 130 does not rotate relative to the cap 130 and, as a result, the contact pin 55 will not be rotate relative to the rest of the assembly 120 or the rest of the lead connector end 35.

In other versions of the embodiments depicted in FIGS. 13-21 where the contact pin 55 is fixed to or integrally formed with the cap 130 such that the contact pin 55 will not rotate relative to the cap 130, the cap 130 may be rotatably attached to the collar 125 such that a bearing arrangement may exist between the cap 130 and the collar 130. Specifically, the wings 167 may retain the cap 130 with in the collar 125 but the surfaces of the wings 167 may form a bearing arrangement with the mating surfaces of the collar 125. As a result, the contact pin 55 and cap 130 may rotate as a unit relative to the collar 125 and the rest of the assembly 120 or the rest of the lead connector end 35.

As discussed earlier, depending on which components (i.e., contact pin 55, cap 130 and collar 125) are rotatable relative to each other, the components 55, 130, 125 may be formed from a variety of materials. For example, if the pin 55 is rotatably coupled to the cap 130 and the cap 130 is non-rotatably coupled to the collar 125, the cap 130 may be formed from a non-metallic material and the collar 125 may be formed from a metallic or non-metallic material. As another example, if the pin 55 is non-rotatably coupled to the cap 130 and the cap 130 is rotatably coupled to the collar 125, the cap 130 may be formed from a metallic material and the collar 125 may be formed from a non-metallic material. As yet another example, if the pin 55 is non-rotatably coupled to the cap 130 and the cap 130 is rotatably coupled to the collar 125, the cap 130 may be formed from a non-metallic material and the collar 125 may be formed from a metallic or non-metallic material. Other combinations may be available as long as adjacent rotating parts (e.g., the pin 55 rotatable relative to the cap 130 or the cap 130 rotatable relative to the collar 125) are not both formed of a metallic material, thereby avoiding the possibility of electrical chatter resulting from adjacent metallic surfaces rotating against each other. Where the pin 55, cap 130 and collar 125 are all coupled together in a non-rotatable fashion, the cap 130 and collar 125 may be both formed of metallic material, both formed of non-metallic material, or formed of a combination of metallic and non-metallic material.

Although the present invention has been described with reference to preferred embodiments, persons skilled in the art will recognize that changes may be made in form and detail without departing from the spirit and scope of the invention.

What is claimed is:

1. An implantable medical lead comprising:
   a body including a distal portion and a proximal portion;
   at least one electrode on the distal portion; and
   a lead connector end on the proximal portion and including:
   body portion at least partially formed of a polymer material;
   a pin contact electrically coupled to the at least one electrode and proximally extending from the lead connector end; and
   a retainer assembly retaining the pin contact as part of the lead connector end and including a collar imbedded in the polymer material and a cap secured within the collar via an interference fit arrangement and including a hole through which the pin contact extends.

2. The implantable medical lead of claim 1, wherein the hole of the cap and the pin contact form a bearing arrangement wherein the pin contact is rotatable within the hole.

3. The implantable medical lead of claim 1, wherein the polymer material includes at least one of PEEK and Tecothane.

4. The implantable medical lead of claim 1, wherein the collar is formed from a machinable metal material.

5. The implantable medical lead of claim 1, wherein the collar comprises a hole including an inner surface including a proximal lip, a distal ridge, and a space defined between the lip and ridge, and wherein the cap includes a biased feature that expands in the space when the cap is received within the collar.

6. The implantable medical lead of claim 1, wherein the cap and collar each include structures that combine to form the interference fit arrangement, the cap structure being biased to expand to engage the collar structure when the cap is received within the collar.

7. The implantable medical lead of claim 6, wherein the cap structure includes at least one wing extending both proximally and radially outward.

8. The implantable medical lead of claim 7, wherein the collar structure includes a radially inward projecting lip that is engaged by the at least one wing in forming the interference fit arrangement.

9. The implantable medical lead of claim 8, wherein the at least one wing includes a distal inclined face that engages a proximal portion of the collar when the cap is in the process of being received in the collar, the engagement of the distal inclined face with the proximal portion of the collar causing the at least one wing to displace radially inward.

10. The implantable medical lead of claim 1, wherein the cap includes at least one feature that snaps into engagement with a feature of the collar when the cap is received by the collar.

11. The implantable medical lead of claim 1, wherein the cap and the pin contact are non-rotatable relative to each other.

12. The implantable medical lead of claim 11, wherein a bearing arrangement is formed between the cap and collar so the cap and pin may rotate as a unit relative to the collar.

13. The implantable medical lead of claim 11, wherein the cap and collar are non-rotatable relative to each other.

14. An implantable medical lead comprising:
   a body including a distal portion and a proximal portion;
   at least one electrode on the distal portion; and
   a lead connector end on the proximal portion and including:
   a body portion at least partially formed of a polymer material;
   a pin contact electrically coupled to the at least one electrode and proximally extending from the lead connector end; and
   a retainer assembly retaining the pin contact as part of the lead connector end and including a collar imbedded in the polymer material and a cap secured within the collar via a weld and including a hole through which the pin contact extends.

15. The implantable medical lead of claim 14, wherein the collar includes a hole having an inner circumferential surface, the cap includes an outer circumferential surface, the cap is received in the hole of the collar, the respective circumferential surfaces matingly abutting each other, and the weld extending along a seam formed between the matingly abutting circumferential surfaces.

16. The implantable medical lead of claim 14, wherein the polymer material includes at least one of PEEK and Tecothane.

17. The implantable medical lead of claim 14, wherein the hole of the cap and the pin contact form a bearing arrangement wherein the pin contact is rotatable within the hole.

18. The implantable medical lead of claim 14, wherein the cap and the pin contact are non-rotatable relative to each other.

19. An implantable medical lead comprising:
a body including a distal portion and a proximal portion;
at least one electrode on the distal portion; and
a lead connector end on the proximal portion and including:
a body portion at least partially formed of a polymer material;
a pin contact electrically coupled to the at least one electrode and proximally extending from the lead connector end; and
a retainer assembly retaining the pin contact as part of the lead connector end and including a cap operably coupled to the polymer material via a threaded arrangement and including a hole through which the pin contact extends;
wherein the cap includes self-taping threads that directly thread into the polymer material; and
wherein the cap includes threads and wherein the retainer assembly further includes a collar imbedded in the polymer material and including threads that are threadably engaged by the threads of the cap when the cap is received in the collar.

20. The implantable medical lead of claim 19, wherein the cap further includes at least one of a female engagement feature and a male engagement feature that can be engaged by at least one of a screw driver and wrench.

21. The implantable medical lead of claim 19, wherein the hole of the cap and the pin contact form a bearing arrangement wherein the pin contact is rotatable within the hole.

22. A method of assembling a lead connector end for an implantable medical lead, the method comprising:
providing a lead connector end including a body portion at least partially formed of a polymer material and a collar imbedded in the polymer material;
providing a cap including at least one feature configured to create an interference fit with at least one feature of the collar;
inserting a pin contact through a hole in the cap; and
creating the interference fit between the cap and collar by inserting the cap into the collar.

23. The method of claim 22, wherein creating the interference fit includes the at least one feature biasing into an expanded condition within the collar.

24. The method of claim 22, wherein creating the interference fit includes the at least one feature snapping into engagement with the at least one feature of the collar.

25. The method of claim 22, wherein creating the interference fit includes causing a portion of the at least one feature of the cap to engage a portion of the collar when the cap is in the process of being received in the collar, the engagement of the at least one feature of the cap with the portion of the collar causing the at least one feature of the cap to displace radially inward.

26. The method of claim 25, wherein once the at least one feature of the cap clears the portion of the collar, the at least one feature of the cap biases radially outward into an expanded state to engage the at least one feature of the collar.

* * * * *